United States Patent
Chang et al.

(10) Patent No.: US 6,846,632 B2
(45) Date of Patent: Jan. 25, 2005

(54) METHOD FOR RAPIDLY IDENTIFYING PORCINE ESTROGEN RECEPTOR MARKER

(75) Inventors: Hsiu-Luan Chang, Tainan (TW); Ren-Bao Liaw, Tainan (TW); Ming-Che Wu, Tainan (TW)

(73) Assignee: Cheng-Taung Wang, Tainan (TW)

( * ) Notice: Subject to any disclaimer, the term of this patent is extended or adjusted under 35 U.S.C. 154(b) by 456 days.

(21) Appl. No.: 10/100,141

(22) Filed: Mar. 19, 2002

(65) Prior Publication Data

US 2003/0190619 A1 Oct. 9, 2003

(51) Int. Cl.$^7$ ................................................. C12Q 1/68
(52) U.S. Cl. ...................... 435/6; 435/91.2; 435/91.21; 536/23.1; 536/24.3; 536/24.31; 536/24.33
(58) Field of Search ................... 435/6, 91.2; 536/23.1, 536/24.3, 24.31, 24.33

Primary Examiner—Jeffrey Fredman
Assistant Examiner—Heather G. Calamita
(74) Attorney, Agent, or Firm—Rosenberg, Klein & Lee

(57) ABSTRACT

A method for rapidly identifying porcine estrogen receptor (ESR) marker comprises using published primers to amplify the target DNA fragment by polymerase chain reaction (PCR). The DNA fragment is cloned and then sequenced. The key positions of the sequence are modified to generate three primers which are used to amplify different DNA fragments with different genotypes by PCR to eliminate extra restriction cut reaction. A long one of the primers is to specifically amplify non-prolific allele, a short one of the primers is to specifically amplify prolific allele, and the remaining one is mutual and complimentary to the sequence. After PCR and electrophoresis, the sample with 90 bp band is identified as prolific genotype, the sample with 110 bp band is identified as non-prolific genotype, and the sample with 90 bp and 110 bp bands is identified as heterogenotype.

3 Claims, 4 Drawing Sheets extracting DNA polymerase chain reaction electrophoresis identification

```
            10          20          30          40
            |           |           |           |
  1  CCTGTTTTACAGTGACTTTACAGAGTATATCTAAAGATG

41  CAGAATCAAGTTTTATGAGAC<u>AGCT</u>GTTCTTGTCAAGTC

81  CCCATTCCACCCTATTCTAATTGGACTGACCCTCGAAGTG
```

FIG. 2

```
              10             20             30            40
               |              |              |             |
  1  CCTGTTTTACAGTGACTTTTACAGAGTATATCTAAAGATG

41  CAGAATCAAGTTTTATGAGACCAACTTTTCTTGTCAAGTC

81  CCATTCCACCCTATTCTAATTGGACTGACCCTCGAAGTG
```

FIG. 3

SEQUENCE LISTING

<160> NUMBER OF SEQ ID NOS: 3

<210> SEQ ID NO 1
<211> LENGTH: 48
<212> TYPE: DNA
<213> ORGANISM: Sus sp.

<400> SEQUENCE: 1
gtcagtccaa ttagaatagg gcgggaatgg ggacttgaca agaaacgt            48

<210> SEQ ID NO 2
<211> LENGTH: 27
<212> TYPE: DNA
<213> ORGANISM: Sus sp.

<400> SEQUENCE: 2
gtggaatggg gacttgacaa gaacacc            27

<210> SEQ ID NO 3
<211> LENGTH: 30
<212> TYPE: DNA
<213> ORGANISM: Sus sp.

<400> SEQUENCE: 3
cctgttttac agtgactttt acagagtata            30

METHOD FOR RAPIDLY IDENTIFYING PORCINE ESTROGEN RECEPTOR MARKER

BACKGROUND OF THE INVENTION

1. Field of the Invention

The present invention relates to a method for rapidly identifying porcine estrogen receptor (ESR) marker at a low cost. In particular, the present invention relates to a method for rapidly identifying porcine estrogen receptor marker by means of mutagenically separated polymerase chain reaction (MSPCR).

2. Description of the Related Art

It is a trend to raise as many pigs as possible in a limited area to improve the productivity. Improvement in the productivity of female pigs will definitely decrease the cost and increase the competitiveness. In addition to breeding, a marker-assisted selection has been used to sort pigs with high productivity. The number of pups for a female pig at each birth is an important index for its propagating capability. Researches in the genes affecting the number of pups are undergoing, and examples of which are disclosed in "Estrogen Receptor Gene, ESR," Rothschild et al., Anim. Genet, Volume 22, page 448, 1991; Proc. 5$^{th}$ World Congr. Gene t. Appli. Livest. Prod. Volume 21, pages 225–228, 1994; Proc. Natl. Acad. Sci. USA, Volume 93, pages 201–205, 1996; Short et al., J. Anim. Sci. Volume 73, (Suppl. 1), page 109 (Abstr.), 1995; J. Anim. Sci. Volume 7-5 (Journal 12), pages 3138–3142, 1997; "Major Histocompatibility Complex Genes, MHC," Warner and Rothschild, Immunogenetics of the MHC, pages 368–397, VCH Publishers, New York, USA, 1991; and "Osteopontin Marker, OPN," Short et al., J. Anim. Sci. Volume 75 (Suppl. 1), page 29 (Abstr.), 1997. All of these documents are related to propagating capability.

The ESR gene on the short arm of the No. 1 chromosome comprises two alleles A and B. According to research, the allele B is the primary gene for the productivity of the "May-San" pigs. When existing in homozygote state, the major histocompatibility complex genes (MHC) shall adversely affect survival of the embryos. The genotypes of the osteopontin markers (OPN) affect the total number of pups at a birth and the number of survival pups, wherein one of five alternate genes relates to the total number of pups at a birth, and the other four alternate genes relate to the number of survival pups. According to research, the survival rate of pups from the first birth through the sixth birth is relatively high for female pigs of OPN hetero-genotype. (Liao, Zen-Po et al., Chinese Livestock Magazine, Volume 28(1), pages 33–39, 1999).

According to Applicant's own research in examination of the pigs in the slaughterhouses, no homozygote with allele B was found, and the percentage of zygote with allele AB was 17.8%; namely, not many studpigs in Taiwan As possess allele B. According to research in the studpigs, the estrogen receptor (ESR) inheriting marker is indeed relevant to the propagating capability. According to primary research, the survival pigs bred by a female pig with prolific genotype was higher than those bred by a female pig without prolific genotype by 0.39 at the first birth, and by 0.31 at each subsequent birth. Thus, it would be able to reduce the number of new spare studpigs that have to be raised while achieving the same productivity, reducing the cost, and improving the competitiveness if the estrogen receptor genotype of each pig can be identified when it is still a pup. Currently in the art, polymerase chain reaction and restriction cut reaction are used to fragment DNA to thereby identify the genotype of pigs, but it is time consuming and costly.

SUMMARY OF THE INVENTION

An object of the present invention is to provide a method for rapidly identifying porcine estrogen receptor marker by means of mutagenically separated polymerase chain reaction (MSPCR).

A method for rapidly identifying porcine estrogen receptor (ESR) marker comprises using published primers to amplify the target DNA fragment by polymerase chain reaction (PCR). The DNA fragment is cloned and then sequenced. The key positions of the sequence are modified to generate three primers which are used to amplify different DNA fragments with different genotypes by PCR to eliminate extra restriction cut reaction. A long one of the primers is to specifically amplify non-prolific allele, a short one of the primers is to specifically amplify prolific allele, and the remaining one is mutual and complimentary to the sequence. After PCR and electrophoresis, the sample with 90 bp band is identified as prolific genotype, the sample with 110 bp band is identified as non-prolific genotype, and the sample with 90 bp and 110 bp bands is identified as heterogenotype.

Other objects, advantages, and novel features of the invention will become more apparent from the following detailed description when taken in conjunction with the accompanying drawings.

BRIEF DESCRIPTION OF THE DRAWINGS

FIG. 2 is a diagram illustrating a fragment of a DNA sequence of a prolific allele of a pig, wherein the sequence of the sixty-second position through the sixty-seventh position is CAGCTG, which is to be identified and fragmented by the restriction enzyme Puv II.

FIG. 3 is a diagram illustrating a fragment of a DNA sequence of a non-prolific allele of a pig, wherein the sequence of the sixty-second position through the sixty-seventh position is CAACTT, which is cannot be identified and fragmented by the restriction enzyme Puv II.

DETAILED DESCRIPTION OF THE PREFERRED EMBODIMENT

Figure 1:
FIG. 1 is a flowchart of a method for rapidly identifying porcine estrogen receptor marker in accordance with the present invention.
Figure 1:
Figure 1:

The present invention provides a method for rapidly identifying porcine estrogen receptor marker by means of mutagenically separated polymerase chain reaction (MSPCR). As illustrated in FIG. 1, a first step of the method in accordance with the present invention comprises extracting a DNA sample from a pig to be identified. The DNA sample is extracted from blood, internal organs, muscular tissues, or semen. The DNA sample of 20~25 ng is then combined with a solution comprising dNTP (deoxynucleotide-triphosphates) of 0.4 mM, a first primer A1 of 0.05 μM a second primer B1 of 0.1 μM, a third primer R1 of 0.2 μM, MgCl$_2$ of 3 mM, 1×PCR buffer solution (including Tris-HCl of 20 mM, KCl of 50 mM, PH 8.4), and one unit of taq DNA polymerase. The total volume for the reactive substance is preferably 10 μL.

The first primer A1 has a DNA sequence as follows:

5'-GTCAGTCCAATTAGAATAGGGCGGGAATGGGGACTTGACAAG

AAACGT-3'

The second primer B1 has a DNA sequence as follows:
5'-GTGGAATGGGGACTTGACAAGAACACC-3'.
The third primer R1 has a DNA sequence as follows:
5'-CCTGTTTTACAGTGACTTTTACAGAGTATA-3'.

In the first cycle of the mutagenically separated polymerase chain reaction (MSPCR), the temperature and time are set as follows: 94° C., 60 seconds; 67° C., 60 seconds; 72° C., 60 seconds. The temperature and time in the next cycle are set as follows: 94° C., 30 seconds; 67° C., 45 seconds; 72° C., 45 seconds. The error for the time is ±5%, and the error for the temperature is ±3° C. The cycles last for forty (40) times, and an prolonged reaction is held for ten (10) minutes at 72° C.

Figure 4:
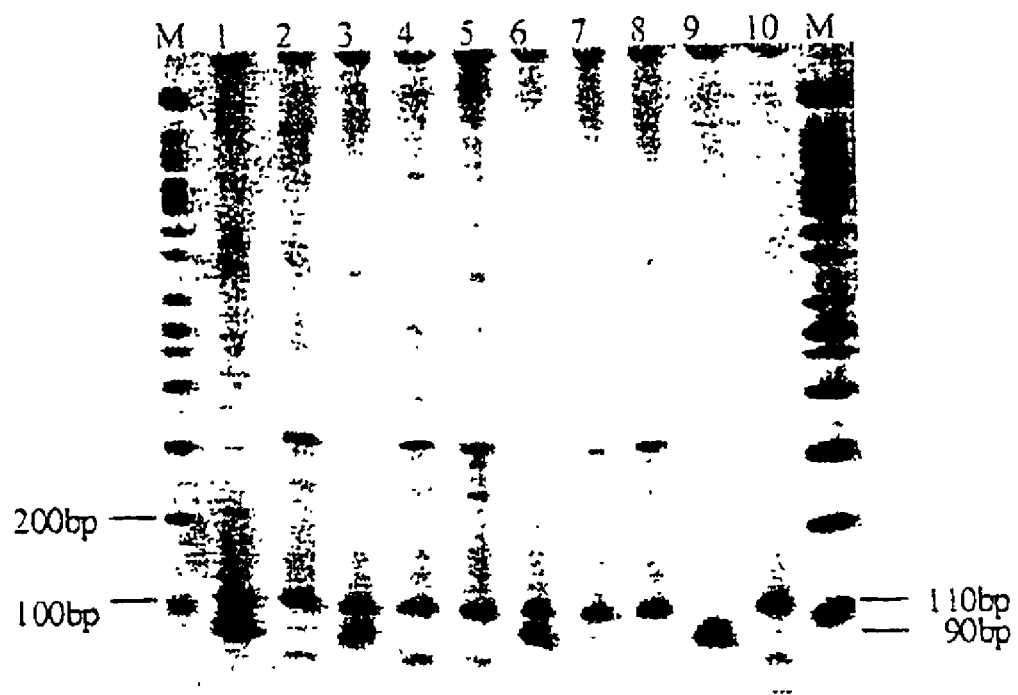
FIG. 4 is a diagram illustrating inspection of the prolific genotype inherited marker, wherein M denotes large/small, the samples in the first, third, and sixth columns are heterogenotype, the samples in the second, fourth, fifth, seventh, eighth, and tenth columns are non-prolific genotype, and the samples in the ninth column are prolific genotype.

The product resulting from the polymerase chain reaction (PCR) is treated with electrophoresis and then dyed to provide phases. The sample with 90 bp band is identified as prolific genotype, the sample with 110 bp band is identified as non-prolific genotype, and the sample with 90 bp and 110 bp bands is identified as hetero-genotype (see FIG. 4).

Thus, the genotype of the pig can be identified by the band of the product in one polymerase chain reaction, subject to the above-mentioned condition.

During the identification by the polymerase chain reaction using the three primers A1, B1, and R1, the amplified products possess different bands according to their genotypes. Thus, the step of restriction cut reaction can be eliminated. The reactive condition is obtained after numerous tests. When compared to the current identifying method (Rothschild et al., Proc. Natl. Sci. USA 93: 201–205, 1996) under the same background for identification, the cost for identification is saved by at least ⅕ and the time for identification is saved by at least ⅓ when using the method in accordance with the present invention.

Although the invention has been explained in relation to its preferred embodiment, it is to be understood that many other possible modifications and variations can be made without departing from the scope of the invention as hereinafter claimed.

What is claimed is:

1. A method for rapidly identifying porcine estrogen receptor marker by a mutagenically separated polymerase chain reaction, the method comprising the steps of:

(a) extracting a DNA sample from a pig to be identified;

(b) proceeding with a polymerase chain reaction by means of combining the DNA sample with a solution comprising dNTP (deoxy-nucleotide-triphosphates), a first primer, a second primer, a third primer, magnesium chloride, buffer solution, and taq DNA polymerase, wherein the first primer has a DNA sequence as follows:

5'-GTCAGTCCAATTAGAATAGGGCGGGAATGGGGACTTG

ACAAGAAACGT-3';

the second primer has a DNA sequence as follows:
5'-GTGGAATGGGGACTTGACAAGAACACC-3'; and
the third primer R1 has a DNA sequence as follows:
5'-CCTGTTTTACAGTGACTTTTACAGAGTATA-3';
and (c) electrophoresizing and dying a product resulting from step (b) to thereby identify the DNA sample by a band of the DNA sample, in which the DNA sample is identified as prolific genotype when having 90 bp band, the sample is identified as non-prolific genotype when having 110 bp band, and the sample is identified as hetero-genotype when having 90 bp bands and 110 bp bands.

2. The method as claimed in claim 1, wherein the DNA sample is of 20~25 ng, the dNTP (deoxy-nucleotide-triphosphates) has a concentration of 0.4 mM, the first primer has a concentration of 0.05 $\mu$M, the second primer has a concentration of 0.1 $\mu$M, the third primer has a concentration of 0.2 $\mu$M, the magnesium chloride has a concentration of 3 mM, the buffer solution includes Tris-HCl of 20 mM, KCl of 50 mM, PH 8.4, the taq DNA polymerase is one unit and the total volume for the reactive substance is preferably 10 $\mu$L.

3. The method as claimed in claim 1, wherein in a first cycle of the mutagenically separated polymerase chain reaction, the temperature and time are set as follows: 94° C., 60 seconds; 67° C., 60 seconds; 72° C., 60 seconds, the error for the time is ±5%, and the error for the temperature is ±3° C. wherein the temperature and time in a next cycle are set as follows: 94° C., 30 seconds; 67° C., 45 seconds; 72° C., 45 seconds, the error for the time is ±5%, and the error for the temperature is ±3° C., and wherein the cycles last for forty times, and an prolonged reaction is held for ten minutes at 72±3° C.

* * * * *